United States Patent
Wogram et al.

(10) Patent No.: US 10,492,963 B2
(45) Date of Patent: Dec. 3, 2019

(54) PACKAGING FOR A MEDICINAL PRODUCT

(71) Applicant: BSN Medical GmbH, Hamburg (DE)

(72) Inventors: Marco Peter Wogram, Hamburg (DE); Sascha Casu, Hamburg (DE)

(73) Assignee: BSN Medical GMBH, Hamburg (DE)

( * ) Notice: Subject to any disclaimer, the term of this patent is extended or adjusted under 35 U.S.C. 154(b) by 36 days.

(21) Appl. No.: 15/743,747

(22) PCT Filed: Jul. 15, 2016

(86) PCT No.: PCT/EP2016/066882
§ 371 (c)(1),
(2) Date: Jan. 11, 2018

(87) PCT Pub. No.: WO2017/009448
PCT Pub. Date: Jan. 19, 2017

(65) Prior Publication Data
US 2018/0200126 A1 Jul. 19, 2018

(30) Foreign Application Priority Data
Jul. 16, 2015 (DE) .......... 10 2015 111 582

(51) Int. Cl.
*A61F 15/00* (2006.01)
*A61F 13/00* (2006.01)
(Continued)

(52) U.S. Cl.
CPC ............ *A61F 15/002* (2013.01); *A01N 59/16* (2013.01); *A61F 13/00063* (2013.01);
(Continued)

(58) Field of Classification Search
CPC ... A01N 59/16; A61F 13/00; A61F 13/00063; A61F 13/00072; A61F 15/00;
(Continued)

(56) References Cited

U.S. PATENT DOCUMENTS 1,963,233 A * 6/1934 Goldstein ............. A61F 15/002
242/146
8,333,743 B2 * 12/2012 Toreki .................... A01N 25/34
427/2.31
(Continued)

FOREIGN PATENT DOCUMENTS

EP 1555944 B1 4/2004
EP 2 113 466 A1 11/2009
(Continued)

OTHER PUBLICATIONS

International Search Report carried out by the European Patent Office dated Nov. 17, 2016 for PCT/EP2016/066882.

*Primary Examiner* — Bryon P Gehman
(74) *Attorney, Agent, or Firm* — Shumaker, Loop & Kendrick, LLP

(57) ABSTRACT

The present invention relates to a reel for a plaster strip roll with one or two side discs and/or a cover/protective ring for a plaster strip roll, which optionally has a tear-off edge, as well as the production thereof. The reel or the cover/protective ring, respectively, comprises an antimicrobially effective substance, wherein, on the outer surface of the reel or of the cover/protective ring, respectively, there is contact between the antimicrobially effective substance and the environment.

20 Claims, 2 Drawing Sheets

(51) Int. Cl.
*A01N 59/16* (2006.01)
*B65B 33/02* (2006.01)
*B65D 85/67* (2006.01)

(52) U.S. Cl.
CPC ........ *A61F 13/00072* (2013.01); *B65B 33/02* (2013.01); *B65D 85/67* (2013.01)

(58) Field of Classification Search
CPC ....... A61F 15/002; B65B 33/02; B65D 85/67; B65D 85/671; B65D 85/672
USPC .................................. 206/389–416
See application file for complete search history.

(56) References Cited

U.S. PATENT DOCUMENTS

| | | | |
|---|---|---|---|
| 9,402,770 B2 * | 8/2016 | Moghe | A61F 13/00063 |
| 2003/0150896 A1 | 8/2003 | Michel | |
| 2010/0055157 A1 * | 3/2010 | Gunn | A61K 33/38 |
| | | | 424/447 |
| 2011/0114640 A1 | 5/2011 | Black | |
| 2014/0242098 A1 * | 8/2014 | Yuan | A61J 1/00 |
| | | | 424/184.1 |

FOREIGN PATENT DOCUMENTS

| | | |
|---|---|---|
| EP | 2428118 A1 | 3/2012 |
| WO | 03024494 A1 | 3/2003 |
| WO | 2004/032704 A2 | 4/2004 |
| WO | 2007/114889 A2 | 10/2007 |

\* cited by examiner

PACKAGING FOR A MEDICINAL PRODUCT

The present invention relates to a packaging for a medicinal product, production and use thereof.

BACKGROUND TO THE INVENTION

In the year 2013 in Germany, the number of deaths caused by infections with pathogenic germs is estimated at more than 15,000 people. A large number of these infections are due to contact contamination with the germs in doctors' surgeries and in hospitals. As these germs are frequently resistant to antibiotics, infections with these germs are particularly problematic, above all for already-weakened patients. In order to reduce a risk of infection through contact contamination, medicinal products are frequently surface-coated with antimicrobially effective substances. Silver is usually used. Silver has a very broad spectrum efficacy even against multiresistant germs, wherein small doses are already sufficient. In addition, antimicrobially effective organic molecules, such as for example polyhexanide or triclosan, are often also used. Furthermore, antimicrobially effective substances based on copper, tin, zinc or titanium are known. Further promising materials are molybdenum- and/or tungsten-containing substances which form an acid medium in the presence of water. Such substances are known, for example from EP 2 428 118 A2.

As already stated, the medicinal products themselves are frequently provided with antimicrobial substances, whereas the packagings of these products are not, as a rule, antimicrobially effective. In the case of frequent contact with the packaging, this leads to a high concentration of germs being able to form on the outside of the packaging in close proximity to the medicinal product. This is the case in particular with a plaster strip roll which is usually on a reel, and is protected against contact with the environment with a cover/protective ring. In practical use, the plaster strip roll is frequently transported in the uniform pocket, where it is in frequent contact with the environment, in particular the hands of the medical staff. The same plaster strip roll is usually used for a large number of patients. The germs thus transferred onto the reel or the cover/protective ring, can then easily be inadvertently transferred onto the patient by the medical staff or the patient. This can lead to serious infections. The risk of such a contact contamination could be substantially reduced, if not prevented, by an antimicrobial finishing of the reel or of the cover/protective ring.

From EP 2 113 466 A1 a tube provided with silver is known which, among other things, can be used for packaging pharmaceutical products such as, for example, healing ointments.

Furthermore, from EP 1 555 944 B1, packaged medicinal products are known, which have a packaging the inside of which has an antimicrobial coating.

DESCRIPTION OF THE INVENTION

The object of the invention is to provide a packaging for a medicinal product in the form of a reel for a plaster strip roll with one or two side discs (hereinafter called "reel") and/or of a cover/protective ring of a plaster strip roll (hereinafter called "cover/protective ring"), which optionally has a tear-off edge, the outer surface of which is free of germs in the case of normal use, or at least has a reduced number of germs in comparison with customary reels or covers/protective rings of a plaster strip roll that are not antimicrobially finished, and maintains this germ-free or germ-reduced state over a longer period. To this end, the reel and/or the cover/protective ring, which optionally has a tear-off edge, is to be finished on the outside with an antimicrobially effective substance, which is/comes into contact with the environment. In addition, the reel or the cover/protective ring, which optionally has a tear-off edge, can be produced as cost-effectively and simply as possible.

These objects are achieved by a packaging for a medicinal product in the form of a reel and/or a cover/protective ring, which optionally has a tear-off edge, and which comprises an antimicrobially effective substance, wherein on the outer surface of the reel and/or of the cover/protective ring, there is contact between the antimicrobially effective substance and the environment. Furthermore, these objects are achieved by a method for producing the reel according to the invention and/or the cover/protective ring according to the invention, which optionally has a tear-off edge, in which an antimicrobially effective substance is arranged at least on the outer surface of the reel and/or of the cover/protective ring.

The present invention is described in detail below, with reference to the figures. The figures show only preferred embodiments and in no way limit the invention.

PACKAGING

Figure 1:
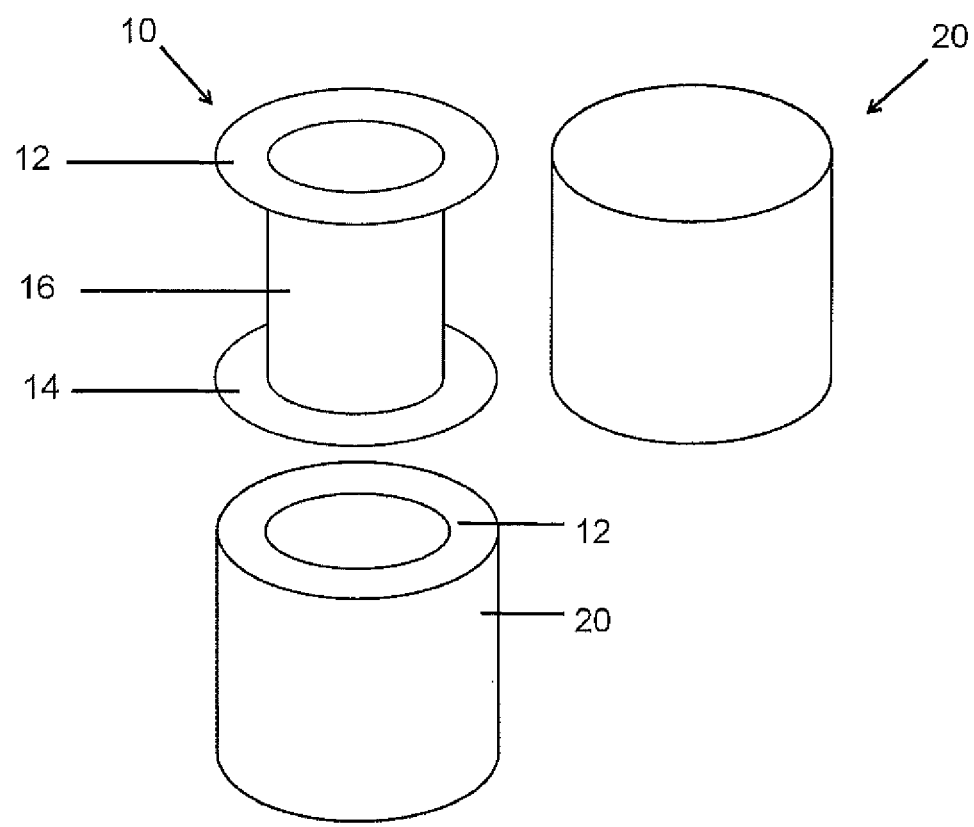
FIG. 1 shows a reel for a plaster strip roll with two side discs and a cover/protective ring for a plaster strip roll in the separated state as well as in the combined state.
Figure 2:
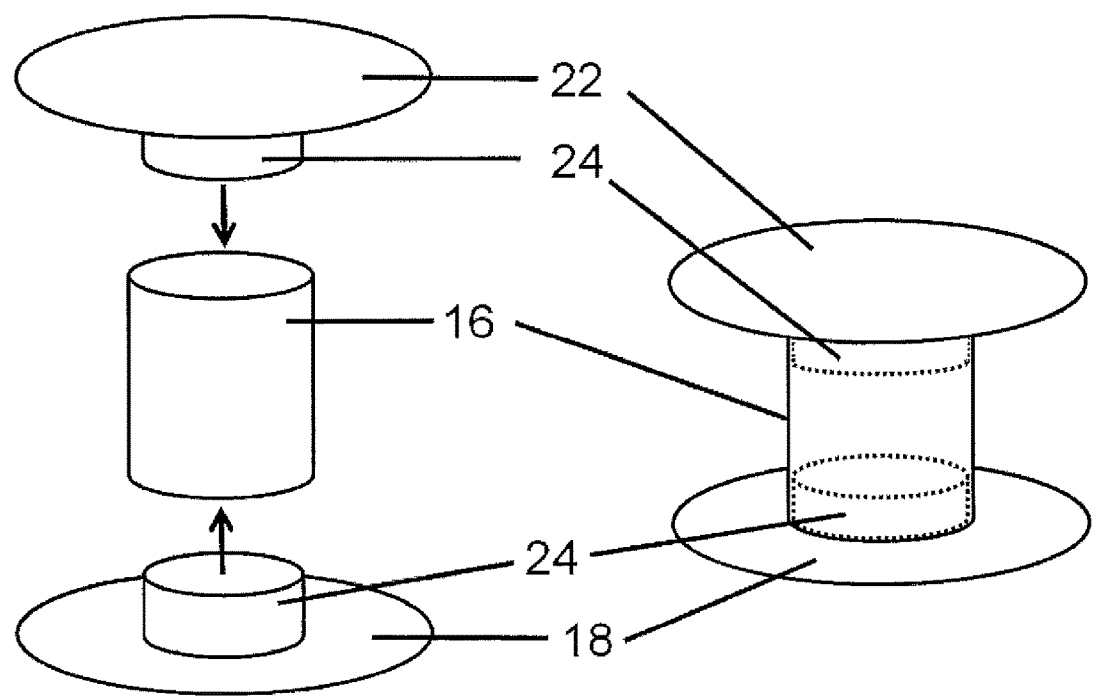
FIG. 2 shows a reel with two side discs detachably connected to the core.

According to the invention, the reel 10 and/or the cover/protective ring 20, which optionally has a tear-off edge, comprises an antimicrobially effective substance, wherein on the outer surface of the reel 10 or of the cover/protective ring 20, there is contact between the antimicrobially effective substance and the environment. A preferred embodiment of the reel according to the invention has two side discs 12, 14 attached to a core 16, wherein the reel is particularly preferably manufactured from one piece ("in a single casting") (FIG. 1). According to another embodiment, the reel comprises a core 16 and two side discs 18, 22 which are detachably connected to the core, and which are attached on both sides of the core 16 by means of a fixing device 24 (FIG. 2). The side discs and optionally also the core are antimicrobially finished. Alternatively, the fixing device 24 and the inside of the core 16 can be formed as interlocking threads, by means of which the side discs 18, 22 are fixed to the core 16. A reel according to the invention can also comprise only one side disc attached to a core. In this case the (protective) function of the other (missing) side disc can be taken over by the cover 20.

The antimicrobially effective substance is not limited to particular substances. For example, metals, metal compounds such as for example salts or oxides, photocatalytically active substances such as for example titanium dioxide or silicon dioxide (silica gel) or organic compounds such as for example triclosan or polyhexanide (PHMB) are suitable. Further suitable organic compounds comprise compounds selected from the group of antistatics, e.g. anionic antistatics, hydrophilizing agents, surfactants such as sulphonates and in particular secondary alkane sulphonates, e.g. $C_{13}$-$C_{17}$-alkane sulphonate sodium salts, in particular $C_{14}$-$C_{17}$-alkane sulphonate sodium salts as well as adsorbents. The antimicrobially effective organic compounds can also be used together with one or more other antimicrobially effective substances.

The antimicrobially effective substance preferably comprises a member of the group consisting of silver, copper, tin, zinc, titanium, molybdenum, tungsten, compounds thereof, an antimicrobially effective organic molecule or any combination thereof. The antimicrobially effective substance preferably comprises one or more tungsten and/or molybdenum compounds.

The antimicrobial effect of a molybdenum- and/or tungsten-containing substance lies in the formation of hydrogen cations, more specifically $H_3O^+$, based on contact with aqueous medium. Thus, for example, molybdenum oxide reacts with water to form molybdic acid ($H_2MoO_4$), which in turn reacts with water to form $H_3O^+$ and $MoO_4^-$ or $MoO_4^{2-}$. The water solubility of the molybdenum- and/or tungsten-containing substances is so low that the substances are virtually not consumed. The antimicrobial effect is thus present almost permanently, but at least for the entire period of use of the reel or of the cover/protective ring. Very small quantities of water, such as e.g. a film only a few nanometres thick, are sufficient for forming the hydrogen cations. The water required for forming the hydrogen cations can, for example, originate from sweat located on hands or from atmospheric humidity.

A silver-containing, antimicrobially effective substance comprises, for example, metallic silver, such as for example colloidal silver, a silver salt, such as for example silver chloride or silver nitrate or silver oxide. A titanium-containing, antimicrobially effective substance preferably contains titanium dioxide. A silicon-containing compound such as silica gel is also suitable, for example. A molybdenum-containing, antimicrobial substance preferably comprises a compound selected from the group consisting of $MoO_3$, $MoO_2$, $ZnMoO_4$, molybdenum nitride, molybdenum carbide, molybdenum silicide, molybdenum sulphide or any combination thereof. A tungsten-containing, antimicrobially effective substance preferably comprises a compound selected from the group consisting of tungsten carbide, tungsten nitride, tungsten silicide, $WO_3$ or any combination thereof. A suitable organic molecule is, for example, selected from the group consisting of triclosan, polyhexanide or a mixture thereof. Furthermore, organic compounds selected from the group of antistatics, e.g. anionic antistatics, hydrophilizing agents, surfactants such as sulphonates and in particular primary or secondary, preferably secondary alkane sulphonates, e.g. $C_{13}$-$C_{17}$-alkane sulphonate sodium salts, in particular $C_{14}$-$C_{17}$-alkane sulphonate sodium salts as well as adsorbents are suitable. The antimicrobially effective organic compounds can also be used together with one or more other antimicrobially effective substances. A combination of the above-named antimicrobial agents is also suitable, such as for example a combination of Mo and/or W with Zn in the form of a compound thereof, or a mixture of compounds thereof, e.g. $ZnMoO_4$ which, in an aqueous environment, also releases the already mentioned $MoO_4^{2-}$, optionally also in combination with, for example, one of the above-named organic compounds, in particular an antistatic, for example a sulphonate such as a primary or secondary $C_{13}$-$C_{17}$-alkane sulphonate sodium salt.

The antimicrobially effective substance is present, for example, in the form of particles. The particle size depends in particular on the antimicrobially effective substance. A person skilled in the art will select the particle size on the basis of their specialist knowledge. If the antimicrobially effective substance contains colloidal silver for example, the latter is preferably present in the form of particles with an average size (diameter) of less than 100 µm, preferably less than 10 µm, more preferably less than 1 µm, even more preferably 1 to 500 nm, in particular 1 to 100 nm. If the antimicrobially effective substance contains $MoO_2$, for example, the latter is preferably present in the form of particles with an average size of from 0.5 to 10 µm, preferably 2 to 8 µm, more preferably 3 to 5, most preferably approximately 3.6 µm. If the antimicrobially effective substance contains $ZnMoO_4$ for example, the latter is preferably present in the form of particles with an average size of from 0.5 to 10 µm, preferably 1 to 8 µm, more preferably 1 to 5, even more preferably 1 to 2 µm, most preferably approximately 1.5 µm. If the antimicrobially effective substance contains $MoO_3$ and/or $WO_3$ for example, the latter is preferably present in the form of particles with an average size of from 5 to 30 µm, preferably 10 to 25 µm, more preferably 13 to 20 µm, most preferably approximately 16 µm. According to the invention, the particle size is determined by means of electron microscopy (REM or TEM). A person skilled in the art will select the particular measurement method based on their specialist knowledge and the particle size. In principle, however, it is true that TEM is rather used for small particles in the nanometre range, and REM rather for larger particles in the micrometre range.

For producing the reel 10 according to the invention and/or the cover/protective ring 20 according to the invention, which optionally has a tear-off edge, paper, cardboard, one or more thermoplastics, one or more thermosetting plastics, one or more elastomers, metal or a mixture thereof, preferably one or more thermoplastics are used as packaging raw material. Such a thermoplastic is preferably selected from the group consisting of acrylonitrile-butadiene-styrene, polyamide, polylactate, polymethyl methacrylate, polycarbonate, polyethylene terephthalate, polyethylene, polypropylene, polystyrene, polyether ether ketone, polyurethane and any combination thereof. The thermoplastic is particularly preferably polystyrene.

The outer surface of the reel 10 or of the cover/protective ring 20 can be completely or partially covered with the antimicrobially effective substance.

The reel 10 or the cover/protective ring 20 can be equipped with the antimicrobially effective substance in that the antimicrobially effective substance is mixed with the packaging raw material before the shaping of the reel 10 or the cover/protective ring 20, and the reel 10 or the cover/protective ring 20 is then shaped from this mixture. The reel 10 or the cover/protective ring 20 is preferably shaped by means of an injection moulding process. In this way, antimicrobially effective substance is exposed on the surface.

In this case, the antimicrobially effective substance is present, as a rule, in a quantity of from 0.1 to 10 wt. %, preferably 0.1 to 5 wt. %, more preferably 0.1 to 3 wt. %, even more preferably 1 to 2.5 wt. %, most preferably 2 wt. % or 1.5 wt. %, relative to the total weight of the reel 10 or of the cover/protective ring 20. If an antimicrobial organic substance optionally in combination with, for example, a molybdenum compound such as $ZnMoO_4$ is used, such as for example an antistatic, the quantity lies in the range of from 0.1 to 10 wt. %, preferably 1.0 to 5 wt. % and preferably 2.5 to 4.0 wt. %, in particular is 3.5 wt. %.

Alternatively, the reel 10 or the cover/protective ring 20 is equipped with the antimicrobially effective substance in that, before the shaping of the reel 10 or of the cover/protective ring 20, no antimicrobially effective substance is present in the packaging raw material, and after shaping, at least the outer surface of the reel 10 or of the cover/protective ring 20 is completely or partially covered with the antimicrobially effective substance. This preferably takes place by means of lacquering, vapour deposition, a spray process, sol-gel technique, printing and/or an immersion process. In this way, at least the outer surface is completely or partially covered with the antimicrobially effective substance.

It is also possible to combine the two finishing variants.

The addition of colouring materials is also possible, in order to effect colouration. Colour masterbatches are for example suitable here, such as the colour masterbatches commercially available from Karl Finke GmbH, e.g. colour masterbatch (Art. No. 626404). The quantity ranges for such colouring materials are from 0.1 to 10 wt. %, preferably 1 to 5 wt. %, e.g. 1.8 wt. %, 2 wt. %, 2.2 wt. % and 3.8 wt. %.

Method

The present invention further relates to a method for producing the reel 10 according to the invention and/or the cover/protective ring 20, which optionally has a tear-off edge, in which an antimicrobially effective substance is arranged at least on the outer surface of the reel 10 or of the cover/protective ring 20.

According to an embodiment, the method is characterized in that packaging raw material is provided and the antimicrobially effective substance is mixed with the packaging raw material in order to form a masterbatch. The mixture of packaging raw material and antimicrobially effective substance (masterbatch) is then shaped into a reel 10 or a cover/protective ring 20, with the result that the antimicrobially effective substance is evenly distributed within the reel 10 or the cover/protective ring 20, as well as being present on the surface thereof. At least on the outer surface, there is contact between the antimicrobially effective substance and the environment. According to the invention, paper, cardboard, one or more thermoplastics, one or more thermosetting plastics, one or more elastomers, metal or any mixture thereof, are used as packaging raw material. The packaging raw material is preferably selected from the group consisting of one or more thermoplastics.

The packaging raw material is particularly preferably selected from the group consisting of acrylonitrile-butadiene-styrene, polyamide, polylactate, polymethyl methacrylate, polycarbonate, polyethylene terephthalate, polyethylene, polypropylene, polystyrene, polyether ether ketone, polyurethane and any combination thereof. In particular, the packaging raw material is polystyrene.

The masterbatch can be directly shaped into a reel 10 or a cover/protective ring 20, which optionally has a tear-off edge. The antimicrobially effective substance is mixed with the packaging raw material or already incorporated during the production of the packaging raw material, for example in a quantity of from 0.1 to 10 wt. %, preferably 0.1 to 5 wt. %, more preferably 0.1 to 3 wt. %, even more preferably 1 to 2.5 wt. %, most preferably 2 wt. % or 1.5 wt. %, relative to the total weight of the masterbatch.

The masterbatch can also be mixed with further packaging raw material or further antimicrobially effective substance before the shaping. Here, the weight ratios of antimicrobially effective substance to packaging raw material are set such that the antimicrobially effective substance is present in the reel 10 obtained, or the cover/protective ring 20 obtained, in a quantity of from 0.1 to 10 wt. %, preferably 0.1 to 5 wt. %, more preferably 0.1 to 3 wt. %, even more preferably 1 to 2.5 wt. %, most preferably 2 wt. % or 1.5 wt. %, relative to the total weight of the reel 10 or cover/protective ring 20 obtained after the shaping, which optionally has a tear-off edge. Such a masterbatch to be mixed with further packaging raw material (and optionally further antimicrobially effective substance) is more concentrated and contains, for example, 10 to 30 wt. %, preferably 20 wt. % of the antimicrobially effective substance. The desired concentration in the end product is then set during mixing with the further packaging raw material.

The reel 10 or the cover/protective ring 20 is preferably shaped by means of an injection moulding process. In this case the packaging raw material preferably comprises one or more thermoplastics, preferably a member of the group consisting of acrylonitrile-butadiene-styrene, polyamide, polylactate, polymethyl methacrylate, polycarbonate, polyethylene terephthalate, polyethylene, polypropylene, polystyrene, polyether ether ketone, polyurethane and any combination thereof, particularly preferably polystyrene.

Alternatively, before the shaping of the reel 10 or of the cover/protective ring 20, no antimicrobially effective substance is present, with the result that initially, a reel or a cover/protective ring is formed, which is free of antimicrobially effective substance. In this case, at least the outer surface of the shaped reel 10 or of the cover/protective ring 20 is covered with the antimicrobially effective substance by means of lacquering, vapour deposition, a spray process, sol-gel technique, printing and/or an immersion process, with the result that at least the outer surface is completely or partially covered with the antimicrobially effective substance. The antimicrobially effective substance is present in a quantity of from 0.1 to 10 wt. %, preferably 0.1 to 5 wt. %, more preferably 0.1 to 3 wt. %, most preferably 2 wt. % in the application medium, for example lacquer. In this case the reel 10 or the cover/protective ring 20 is also manufactured from paper, cardboard, one or more thermoplastics, one or more thermosetting plastics, one or more elastomers, metal or any mixture thereof, preferably from one or more thermoplastics, particularly preferably from acrylonitrile-butadiene-styrene, polyamide, polylactate, polymethyl methacrylate, polycarbonate, polyethylene terephthalate, polyethylene, polypropylene, polystyrene, polyether ether ketone, polyurethane and any combination thereof, in particular from polystyrene.

The two finishing variants can also be combined.

The antimicrobially effective substance is preferably used in the form of particles. Alternatively, the coating can also be present particle-free, for example in the form of a film. Particle-free coatings can be formed, for example, by means of lacquering, vapour deposition, printing or sol-gel processes.

The reel according to the invention or the cover/protective ring according to the invention is particularly suitable for use for reducing the risk of infection through contact contamination, in particular in doctors' surgeries or hospitals.

EMBODIMENT EXAMPLES

Example 1

200 g polystyrene (High Impact 6540 from Total Petrochemicals) is mixed with 800 g $MoO_2$ (particle size 3.6 µm). A masterbatch is produced from this mixture by means of extrusion and subsequent granulation. 25 g of the masterbatch obtained is mixed with 975 g polystyrene and again extruded and subsequently granulated. The material thus obtained is shaped into a reel with two side discs 10 and a cover/protective ring 20 by means of injection moulding processes.

Example 2

200 g polystyrene (High Impact 6540 from Total Petrochemicals) is mixed with 800 g $WO_3$ (particle size 16 µm).

A masterbatch is produced from this mixture by means of extrusion and subsequent granulation. 25 g of the masterbatch obtained is mixed with 975 g polystyrene and again extruded and subsequently granulated. The material thus obtained is shaped into a reel with two side discs 10 and a cover/protective ring 20 by means of injection moulding processes.

Example 3

200 g polystyrene (High Impact 6540 from Total Petrochemicals) is mixed with 400 g $MoO_2$ (particle size 3.6 μm) and 400 g $WO_3$ (particle size 16 μm). A masterbatch is produced from this mixture by means of extrusion and subsequent granulation. 25 g of the masterbatch obtained is mixed with 975 g polystyrene and again extruded and subsequently granulated. The material thus obtained is shaped into a reel with two side discs 10 and a cover/protective ring 20 by means of injection moulding processes.

Example 4

1000 g polystyrene (High Impact 6540 from Total Petrochemicals) is mixed with 250 g $ZnMoO_4$ (particle size 1-1.5 μm). A masterbatch is produced from this mixture by means of extrusion and subsequent granulation. 375 g of the masterbatch obtained is mixed with 4350 g polystyrene (High Impact 6540 from Total Petrochemicals), 175 g antistatic (Atmer 190 from Croda; CAS 85711-69-9; EINECS 288-330-3) and 60 g colour masterbatch (Art. No. 626404 from Karl Finke GmbH) and shaped into a reel with two side discs 10 and a cover/protective ring 20 by means of injection moulding processes.

Example 5

1000 g polystyrene (High Impact 6540 from Total Petrochemicals) is mixed with 250 g $ZnMoO_4$ (particle size 1-1.5 μm). A masterbatch is produced from this mixture by means of extrusion and subsequent granulation. 625 g of the masterbatch obtained is mixed with 4100 g polystyrene (High Impact 6540 from Total Petrochemicals), 175 g antistatic (Atmer 190 from Croda; CAS 85711-69-9; EINECS 288-330-3) and 60 g colour masterbatch (Art. No. 626404 from Karl Finke GmbH) and shaped into a reel with two side discs 10 and a cover/protective ring 20 by means of injection moulding processes.

Example 6

1000 g polystyrene (High Impact 6540 from Total Petrochemicals) is mixed with 250 g $ZnMoO_4$ (particle size 1-1.5 μm). A masterbatch is produced from this mixture by means of extrusion and subsequent granulation. 625 g of the masterbatch obtained is mixed with 4160 g polystyrene (High Impact 6540 from Total Petrochemicals) and 175 g antistatic (Atmer 190 from Croda; CAS 85711-69-9; EINECS 288-330-3) and shaped into a reel with two side discs 10 and a cover/protective ring 20 by means of injection moulding processes.

Example 7

1000 g polystyrene (High Impact 6540 from Total Petrochemicals) is mixed with 250 g $ZnMoO_4$ (particle size 1-1.5 μm). A masterbatch is produced from this mixture by means of extrusion and subsequent granulation. 375 g of the masterbatch obtained is mixed with 4350 g polystyrene (High Impact 6540 from Total Petrochemicals), 175 g antistatic (Heco Stat 290 from Hecoplast GmbH; CAS 97489-15-1; EINECS 307-055-2) and 60 g colour masterbatch (Art. No. 626404 from Karl Finke GmbH) and shaped into a reel with two side discs 10 and a cover/protective ring 20 by means of injection moulding processes.

In all the above examples, the commercially available polystyrene "High Impact, Empera 524N" from Ineos Nova can also be used as an alternative.

The antimicrobial effectiveness of the products obtained vis-à-vis *Staphylococcus aureus* and *Pseudomonas aeruginosa* is determined as described in "Materials Science and Engineering: C, Volume 32, Issue 1, 1 Jan. 2012, pages 47-54, paragraph 2.3".

The effectiveness against *Staphylococcus aureus* and *E. coli* can also be shown according to ISO 22196, wherein the following modifications are made:

| ISO 22196 | Deviation |
|---|---|
| Test specimen: flat 50 ± 2 mm × 50 ± 2 mm | Reel produced |
| Covered test surface: 40 ± 2 mm × 40 ± 2 mm | Side disc of the reel produced |
| Incubation time: 24 h | 3 h; 6 h; 24 h |

The cytotoxicity is determined by means of an MTT assay as described in "Materials Science and Engineering: C, Volume 32, Issue 1, 1 Jan. 2012, pages 47-54, paragraph 2.4".

The invention claimed is:

1. Packaging for a medicinal product in the form of a reel for a plaster strip roll with at least one side disc, wherein the packaging comprises an antimicrobially effective substance and, on the outer surface of the packaging, there is contact between the antimicrobially effective substance and the environment.

2. Packaging for a medicinal product according to claim 1, wherein the antimicrobially effective substance comprises at least one member of the group consisting of silver, copper, tin, zinc, titanium, molybdenum, tungsten, silicon, compounds thereof, and an antimicrobially effective organic molecule.

3. Packaging for a medicinal product according to claim 1, wherein the antimicrobially effective substance is present in a quantity of from 0.1 to 10 wt. % relative to the total weight of the packaging.

4. Packaging for a medicinal product according to claim 3, wherein the antimicrobially effective substance is present in a quantity of from 0.1 to 5 wt. % relative to the total weight of the packaging.

5. Packaging for a medicinal product according to claim 3, wherein the antimicrobially effective substance is present in a quantity of from 0.1 to 3 wt. % relative to the total weight of the packaging.

6. Packaging for a medicinal product according to claim 3, wherein the antimicrobially effective substance is present in a quantity of from 0.1 to 2.5 wt. % relative to the total weight of the packaging.

7. Packaging for a medicinal product according to claim 1, wherein the antimicrobially effective substance comprises a compound of at least one of zinc, molybdenum, and tungsten.

8. Packaging for a medicinal product according to claim 7, wherein the antimicrobially effective substance further comprises an antistatic organic compound.

9. Packaging for a medicinal product according to claim 8, wherein the antimicrobially effective substance comprises $ZnMoO_4$ and a sulphonate antistatic.

10. Packaging for a medicinal product according to claim 9, wherein the sulphonate is a secondary $C_{13}$-$C_{17}$-alkane sulphonate sodium salt.

11. Packaging for a medicinal product according to claim 7, wherein the antimicrobially effective substance comprises at least one member of the group consisting of $MoO_2$, $WO_3$ and $ZnMoO_4$.

12. Packaging for a medicinal product according to claim 1, wherein the packaging comprises at least one member of the group consisting of paper, cardboard, one or more thermoplastics, one or more thermosetting plastics, one or more elastomers, and metal.

13. Packaging for a medicinal product according to claim 1, wherein the outer surface of the packaging is at least partially covered with the antimicrobially effective substance.

14. Packaging for a medicinal product according to claim 1, further comprising a cover for the plaster strip roll.

15. Packaging for a medicinal product according to claim 14, wherein the cover has a tear-off edge.

16. Packaging for a medicinal product according to claim 14, wherein the cover is a protective ring.

17. Method for producing the packaging according to claim 1, wherein an antimicrobially effective substance is arranged at least on the outer surface of the packaging.

18. A method of producing the packaging according to claim 17, and including the steps of:
   a2) providing a packaging for the plaster strip roll; and
   b2) applying to at least a portion of the outer surface of the packaging a coating of an antimicrobially effective substance in order to provide an antimicrobial effect to portions of the outer surface of the packaging exposed to the environment.

19. Method according to claim 18, wherein the outer surface of the packaging is coated by at least one member of the group consisting of lacquering, vapour deposition, a spray process, an immersion process, printing, and a sol-gel process.

20. Method for producing a packaging according to claim 17, wherein the antimicrobially effective substance comprises at least one member of the group consisting of silver, copper, tin, zinc, titanium, silicon, molybdenum, tungsten, compounds thereof, an antimicrobially effective organic molecule.

* * * * *